United States Patent [19]

Seifert et al.

[11] Patent Number: 4,942,770
[45] Date of Patent: Jul. 24, 1990

[54] AUTOMATIC ASEPTIC SAMPLING APPARATUS

[76] Inventors: Gunilla K. E. Seifert, R.R. #4, Merrickville, Ontario, Canada, K0G 1N0; Paul P. Matteau, 806-333 Chapel St., Ottawa, Ontario, Canada, K1N 8Y8

[21] Appl. No.: 383,625

[22] Filed: Jul. 24, 1989

[30] Foreign Application Priority Data

Sep. 1, 1988 [CA] Canada ................................. 576514

[51] Int. Cl.$^5$ .............................................. G01N 1/14
[52] U.S. Cl. .................................................. 73/864.34
[58] Field of Search ........... 73/863.83, 863.84, 864.34, 73/864.35, 863.86

[56] References Cited

U.S. PATENT DOCUMENTS 4,037,475 7/1977 Topham ..................... 73/863.83 X
4,307,620 12/1981 Jiskoot ........................ 73/863.83

OTHER PUBLICATIONS

R. C. Dinwoodie et al., A Continuous Method for Monitoring and Controlling Fermentations ..., Biotechnology and Bioengineering, vol. XXVII, pp. 1060–1062 (1985).

M. Ghoul et al, An Automatic and Sterilizable Samples ..., Biotechnology and Bioengineering, vol. XXVIII, pp. 119–121 (1986).

*Primary Examiner*—Tom Noland
*Attorney, Agent, or Firm*—Juliusz Szereszewski

[57] ABSTRACT

There is disclosed a system for taking uniform sterile liquid samples from bioreactors or other containers. The system comprises a three-way valve connected to the bioreactor via a check valve and to a reversible peristaltic pump which is also connected to a waste liquid vessel. The operation of the pump causes, first, the liquid from the bioreactor to be drawn into the system and fill the tubing while excess liquid overflows into the waste liquid vessel. The reverse operation of the pump causes the volume of liquid that remains in the system to be discharged through the three-way valve into a sample receptacle. The return of sampled liquid to the bio-reactor and the contamination of the system from outside are prevented. The system may be operated manually or controlled automatically. It can be useful for sampling of sterile streams e.g. in the food and beverage or pharmaceutical industry.

10 Claims, 1 Drawing Sheet

AUTOMATIC ASEPTIC SAMPLING APPARATUS

This invention is concerned with an automatic aseptic sampling apparatus, especially one suitable for drawing uniform sterile culture samples from a bioreactor at preset intervals.

BACKGROUND OF THE INVENTION

Few sampling systems supplied with laboratory fermenters are easily modified for unattended aseptic sampling. Most commercial sampling systems are manually operated. They are either hooded samplers or bottom-harvesting valves. The former operate on a vaccum principle and are widely accepted as being safe and simple for culture sampling. They can be sterilized either separately or with the culture vessel. During operation, aseptic conditions are maintained by a break in the liquid stream, along with the hood on the exit line. The latter — bottom harvesting valves — are usually found on larger (2–25 L) fermentation vessels. They use in situ steam sterilizable diaphragms or piston valves. These valves are easily sterilized between sampling times and are very reliable.

An automated, computer controlled HPLC system is described by R.C. Dinwoodie et al in Biotechnology and Bioengineering, Vol. XXVII, pp. 1060–1062 (1985). The system is equipped with a continuous flow-through sample vial for the on-line analysis of fermentation broths. A peristaltic pump withdraws a stream from the fermenter, passes it through a filtration unit and then through the vial. The stream and the filtered cells are returned to the fermenter.

Another sampling device is described in Biotechnology and Engineering, Vol. XXVIII, pp. 119–121 (1986) by M. Ghoul et al. This device has a recirculation loop with a proportioning peristaltic pump and four three-way sterilizable valves. A continuous band of ultrafiltration membranes is provided to filter the sample drawn from a fermenter. The filtration surface is renewed after each sample. A cuvette is provided to receive the samples after filtration. The entire sampling system is controlled by a microcomputer. Steam sterilization of the circuit is available to prevent its contamination with microorganisms.

While these prior art devices are useful, there is still a need for a simple and reliable sampling system that is useful, for instance, for batch yeast fermentation lasting 12 to 24 hours. In particular, it is an object of the present invention to develop a sampling system wherein the often large dead volume would be reduced to a minimum.

STATEMENT OF THE INVENTION

According to the present invention, there is provided an apparatus for taking liquid samples from a container such as a bioreactor, or fermenter, which comprises (a) a three-way valve having a first port communicating with the container, a second port and an outlet port, (b) a waste liquid vessel, (c) a reversible pump communicating on its one side with the second port and, on the other side, with the waste liquid vessel, (d) a first flow control means associated with the first port for only permitting the flow of liquid therethrough from the container to the three-way valve, and (e) a second flow control means associated with the outlet port for only permitting the discharge of liquid therethrough from the three-way valve.

Preferably, the reversible pump is a peristaltic pump. A control means is provided to alternate the operation of the pump in both directions. The control means may include, for instance, a timer and a controller which are adapted to operate the pump for a selected period of time at preset intervals in either direction.

DESCRIPTION OF PREFERRED EMBODIMENT

Figure 1:
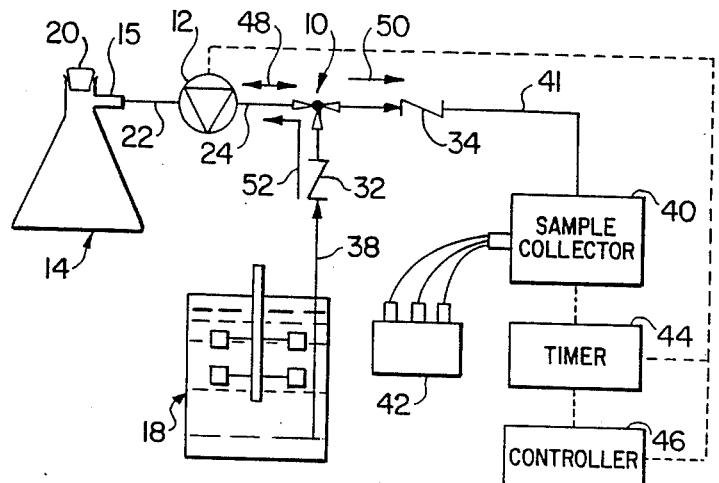
Figure 2:
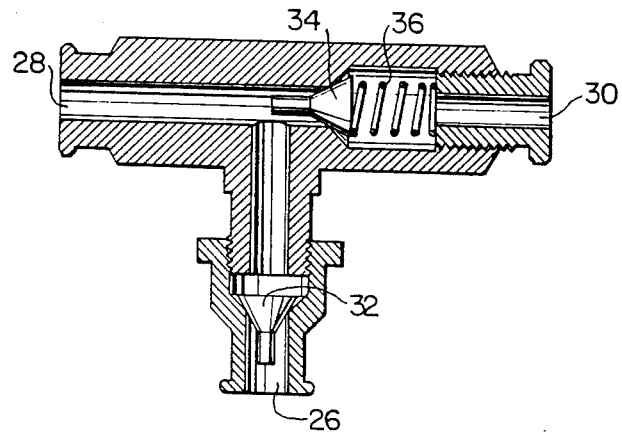

The invention will be explained in more detail in and by the following description to be taken in conjunction with the drawing, in which FIG. 1 is a schematic representation of the invention as associated with a fermenter and FIG. 2 is a cross-sectional view of an embodiment of the three-way valve.

Referring to FIG. 1, the apparatus comprises a three-way valve 10, a reversible peristaltic pump 12, a waste container 14 and a sample collector 40. In the embodiment illustrated, the apparatus is adapted to take uniform liquid samples from a fermenter 18, e.g. to determine the kinetics of fermentation of certain cultures.

The waste container 14 is a simple sterilizable vessel having an inlet port 15. The vessel is provided with a porous plug 20 to prevent the ingress of contaminants, e.g. bacteria to the system while permitting an easy flow of air to and from the container 14.

The peristaltic pump 12 (Cole-Parmer Masterflex Pump with pump head #7015-20) is installed on a length on non-collapsible silicon tubing 22 which connects the port 15 of the waste container 14 to the three-way valve 10. As shown in FIG. 2, the three-way valve 10 has a first port 26, a second port 28 and an effluent port 30. The first port 26 is provided with a check valve 32 which is a sterilizable machined teflon valve but may be replaced with a ball check valve since the branch, or leg, of the valve 10 ending with the first port 26 is normally disposed vertically. The branch of the valve 10 having the outlet port 30 is normally positioned horizontally and is provided with a machined teflon check valve 34 which is held against its seat by means of a spring 36.

The pump 12 is connected to the second port 28 of the three-way valve 10. The first port 26 of the valve 10 is in communication with a fermenter 18 through a conduit 38 which ends with a probe, or a transfer needle, not illustrated in the drawing.

The effluent port 30 is connected to a sample collector 40 via a tubing 41. A Gilson Model 201 programmable fraction collector with a 27-position multipurpose rack has been employed in this embodiment of the invention. The samples are distributed to separate sample tubes situated in a cooling bath 42.

A timer 44 and a controller 46 are coupled electrically with the peristaltic pump 12 and with the sample collector 40. They serve to automate the sampling proce-dure by reversing the operation of the peristaltic pump 12 at selected intervals and by controlling the duration of pumping. Also, the sample collector is controlled correspondingly for the successive samples to be passed to separate sample tubes.

It will be noted that the timer 44 and the controller 46 are not mandatory for the operation of the apparatus. The pump may be operated and reversed manually where only a few samples are to be taken. Alternatively, for long processes to be monitored, it may be expedient to add a computer (a central processing unit) which could be programmed to control the sampling sequences.

While the embodiment described herein features (FIG. 2) a three-way valve incorporating two check valves, it is also conceivable to employ a set-up in which the check valves 32 and 34 would be installed on the lines 38 and 41 respectively, spaced from the three-way valve 10. This alternative, however, adds unnecessary dead volume to the sampling system.

It is relatively easy to determine, by way of a simple test, the volume of liquid that will be discharged from the tubing 22 and the valve 10 after these components have been filled with liquid due to the operation of the pump 12 in the left-hand direction as seen in FIG. 1. That amount of liquid, when the operation of the pump 12 is reversed, will be discharged and its volume will be the volume of a single sample. This total volume, assuming that the volume held within the valve 10 is steady, can be adjusted by changing the length and/or diameter of the tubing 22.

OPERATION OF THE APPARATUS

The sampling procedure may be preceded if necessary, by sterilization of the waste container 14, the three-way valve 10, the check valves 32,34 and the tubings 22 and 38. The tubing 41 does not require sterilization as it will be flushed by liquid from a closed system. After the sterilization is completed and all connections are secured, the peristaltic pump 12 is operated in the "left-hand" direction as seen in FIG. 1. This results in a liquid from the fermenter 18 being drawn through the conduit 38, the first port 26 and the check valve 32, now open, into the three-way valve 10 and on to fill the tubing 22. The check valve 34 is now closed due to the tension in the spring 36. The continuing operation of the pump 12 results in some liquid from the line 22 overflowing into the waste container 14. This ensures that an exact amount of liquid is available for discharge when the operation of the pump is subsequently reversed and also results in the disposal of the stagnant volume ("dead volume") of liquid from valve 10, check valve 32 and tubing 38. The reversal causes a certain overpressure in the line 24 and in the three-way valve. The pressure should be sufficient to open the check valve 34 against the pressure of spring 36 while closing the check valve 32. In this manner, the sampled liquid is prevented from returning to the container. The resulting underpressure created in the waste container 14 draws a corresponding amount of air thereinto. The ensuing risk of contaminating the system by microorganisms from the ambient air is eliminated through the provision of the porous plug 20 or an equivalent filter.

It is evident that the amount of liquid that is held in the vertical leg of the three-way valve 10 (FIG. 2) will not be discharged through the port 30 when the pump 12 operates in its right-hand direction. For that reason, it is advantageous to incorporate the check valve 32 within the three-way valve 10 as close as possible to the other check valve 34.

To facilitate an understanding of the operation of the apparatus, the flow of sample liquid in the system has been illustrated with arrows 48, 50 and 52.

The choice of a peristaltic pump is obviously advantageous in the case where sterility of sampling is of concern, since the design of such pump estimates the contact of mechanical parts with the sampling liquid.

If the fermenter 18 is aerated, a consideration must be given to the gas bubbles that may be carried with the sample into the system and consequently reduce the volume of liquid drawn. In such a case, the inlet of the tubing 38 should be disposed at an area of the fermenter 18 where the amount of dispersed gas in the liquid is minimal.

Another aspect of the aeration is a certain overpressure that develops in the fermenter 18 due to the gas supply and may cause the valve 34 to open at a "wrong" time or even result in the draining of the fermenter. This problem can be virtually eliminated e.g. by the provision of tension adjustment for the spring 36.

The sampling apparatus of the invention can be used for sampling of any sterile stream such as found in the food/beverage industry or in the pharmaceutical industry.

We claim:

1. An apparatus for taking liquid samples from a container, comprising:
    (a) a three-way valve having a first port communicating with the container, a second port and an outlet port,
    (b) a waste liquid vessel,
    (c) a reversible pump communicating on one side thereof with the second port and with the waste liquid vessel on a second side of the pump,
    (d) a first flow control means associated with the first port for only permitting the flow of liquid therethrough from the container to said three-way valve, and
    (e) a second flow control means associated with the outlet port for only permitting the discharge of liquid therethrough from said three-way valve.

2. An apparatus of claim 1 further comprising a control means for operating the reversible pump alternately in reverse directions.

3. An apparatus according to claim 2 wherein the control means includes a timer and a controller, the control means adapted to operate the pump for a selected period of time at preset intervals.

4. The apparatus as set forth in claim 4 wherein the first and second flow control means are check valves associated with the first port and the outlet port of the three-way valve respectively.

5. An apparatus as defined in claims 1, 2 or 3 wherein the pump is a peristaltic pump.

6. An apparatus as defined in claims 1, 2 or 3 further comprising means for preventing the contamination of the liquid from outside.

7. An apparatus as defined in claim 2 or 3 wherein the control means are coupled with a central processing unit.

8. An apparatus as defined in claim 1 wherein the reversible pump is connected to the three-way valve and to the waste liquid vessel with a tubing having a predetermined volume, the volume of the tubing corresponding substantially to the desired volume of the sample.

9. An apparatus as defined in claim 1 further comprising a sample receptacle communicating with the outlet port of the three-way valve.

10. An apparatus as defined in claim 1 wherein said three-way valve, waste liquid vessel and the interconnecting tubing and the flow control means are sterilizable.

* * * * *